United States Patent
Ho et al.

(10) Patent No.: US 6,792,942 B1
(45) Date of Patent: Sep. 21, 2004

(54) SLEEP SILENCER

(76) Inventors: Jung-Hua Ho, 235 Chung-Ho Box 8-24, Taipei (TW); Chiu-Chan Ho, 235 Chung-Ho Box 8-24, Taipei (TW)

( * ) Notice: Subject to any disclaimer, the term of this patent is extended or adjusted under 35 U.S.C. 154(b) by 0 days.

(21) Appl. No.: 10/448,381

(22) Filed: May 30, 2003

(51) Int. Cl.$^7$ .............................................. A61M 15/00
(52) U.S. Cl. .......................... 128/200.24; 128/206.29; 482/13
(58) Field of Search ...................... 128/200.24, 206.29, 128/848, 859, 860; 602/902; 482/13

(56) References Cited

U.S. PATENT DOCUMENTS

| | | | | |
|---|---|---|---|---|
| 90,051 A | * | 5/1869 | Rogers ................... | 128/206.29 |
| 393,869 A | * | 12/1888 | Warren ................... | 128/203.24 |
| 725,354 A | * | 4/1903 | Nicholls ................. | 128/860 |
| 737,008 A | * | 8/1903 | Nichol ................... | 482/13 |
| 957,548 A | * | 5/1910 | Doane .................... | 128/203.24 |
| 1,635,272 A | * | 7/1927 | Härtl .................... | 128/857 |
| 3,298,362 A | * | 1/1967 | Lippitt, Jr. et al. .... | 600/481 |
| 3,333,844 A | * | 8/1967 | Jurschak ................. | 482/13 |
| 3,818,906 A | * | 6/1974 | Stubbs ................... | 606/234 |
| 3,908,987 A | * | 9/1975 | Boehringer ............... | 482/13 |
| 4,054,134 A | * | 10/1977 | Kritzer .................. | 128/205.24 |
| 4,062,358 A | * | 12/1977 | Kritzer .................. | 128/205.24 |
| 4,169,473 A | * | 10/1979 | Samelson ................. | 128/848 |
| 4,170,230 A | * | 10/1979 | Nelson ................... | 128/859 |
| 4,231,364 A | * | 11/1980 | Speshyock ................ | 128/206.15 |
| 4,261,354 A | * | 4/1981 | Nelson ................... | 128/203.23 |
| 4,262,666 A | * | 4/1981 | Nelson ................... | 128/203.23 |
| 4,275,725 A | * | 6/1981 | Nelson ................... | 128/207.14 |
| 4,289,127 A | * | 9/1981 | Nelson ................... | 128/207.14 |
| 4,676,240 A | * | 6/1987 | Gardy .................... | 128/848 |
| 4,770,413 A | * | 9/1988 | Green .................... | 482/13 |
| 4,854,574 A | * | 8/1989 | Larson et al. ............ | 482/13 |
| 5,018,517 A | * | 5/1991 | Liardet .................. | 128/200.24 |
| 5,046,512 A | * | 9/1991 | Murchie .................. | 128/848 |
| 5,154,184 A | * | 10/1992 | Alvarez .................. | 128/848 |
| 5,253,658 A | * | 10/1993 | King ..................... | 128/859 |
| 5,451,190 A | * | 9/1995 | Liardet .................. | 482/13 |
| 5,465,734 A | * | 11/1995 | Alvarez et al. .......... | 128/848 |
| 5,649,540 A | * | 7/1997 | Alvarez et al. .......... | 128/848 |
| 5,715,840 A | * | 2/1998 | Hall ..................... | 128/848 |
| 6,257,238 B1 | * | 7/2001 | Meah ..................... | 128/859 |
| 6,494,209 B2 | * | 12/2002 | Kulick ................... | 128/848 |
| 6,514,176 B1 | * | 2/2003 | Norton ................... | 482/11 |
| 6,581,603 B1 | * | 6/2003 | Schames .................. | 128/848 |

\* cited by examiner

Primary Examiner—Aaron J. Lewis

(57) ABSTRACT

A sleep silencer serves for eliminating snore by holding in a mouth. The sleep silencer comprises a hollow tube which includes a front tube and a rear tube. One end of the front tube has an opening. A periphery of one distal end of the rear tube has a safety ring enclosing the periphery. A ball stop is installed at a center of the opening of the front tube. Two sides of the ball stop are formed with respective turbulent devices which are adhered to an inner wall of the front tube so as to buffer the air in the front tube.

4 Claims, 5 Drawing Sheets

(A)

(B)

SLEEP SILENCER

FIELD OF THE INVENTION

The present invention relates to sleep silencers, and particularly to a sleep silencer by which respiratory passages can be unobstructed. Users only need to hold the sleep silencer in the mouths, snore can be eliminated and thus users can sleep comfortably.

BACKGROUND OF THE INVENTION

Snore is abnormal breath even it is possible to make a person die abruptly. According to the medical research, snore is a state of lacking oxygen transiently, which is harmful to human body. Generally, oxygen is necessary for human body, which provides necessary energy to human body for combustion in the human body. If it occurs in old persons, the persons possibly dies because the breath stops temporarily.

Moreover, other than troubling those slept aside, since snore will cause insufficient oxygen supply, the organs of body are possibly damaged. The greatest impact is the impact of brains since insufficient oxygen supply will induce a great impact to the mechanism of brains. Moreover, if oxygen is insufficient, a greater force is necessary to pump blood to other organs of human body. However this will induce high blood pressure. Thirdly, the testosterone will be insufficient so that the sexual function is reduced. Fourthly, the self-control nerve can not be controlled well and other chronic disease is induced. Furthermore, there are many sicknesses are induced from snores, such as fatness, thick neck, diabetes, cardiopathy, etc.

Snore is induced from nose. Referring to FIG. 1, a nose includes a nasal cavity 10, a nasal bone 11, frontal sinus 12, superior nasal concha 13, middle nasal concha 14, inferior nasal concha 15, sphenoidal sinus 16, etc. Moreover, a mouth 2 includes a soft palate 20, a tongue 21, a pharyngeal wall 22, an anterior palactine arch 23, a uvula 24, vocal cord 25, windpipe 26, esophagus 27, etc. Precisely, snore is induced by palactine arch 23 and uvula 24 or by the drooping of the mucous membrane of respiratory passage so that the respiratory passage becomes narrow. As a result, the air cannot flow unobstructedly and thus in breathing, air flow through the nose or throat so that it is possible that snore is induced as the air is rubbed with the mucous membrane of the respiratory passage so as to induce the mucous membrane or other peripheral organs to vibrate.

Snore will induce a person to be drowsy in daytime and cannot concentrate his (or her) attention.

Currently, there are several ways for eliminating snore.

The first way is by electric knife surgery, or laser surgery, that is to cut off soft palate and uvula. However this will induce a great ache to the patient. Moreover, in a period of about two weeks after operation, mouth and nose are communicable so that water will flow between the two organs. Besides, the swallow will become difficult.

By electric wave surgery, partial anesthesia must be performed to the patient. The patient recovers after several days. Tonsil of the user will reduce so as to have a small volume. However the disease cannot be treated completely. It is possibly reoccurred after a time period.

Snore can also be improved by using electronic stimulation to stimulate the patient, but this will affect the quality of sleep. Moreover, the patient is possibly awake, but he (or she) is difficult to sleep again.

Another method is to use teeth cover, this need a longer time to install the teeth cover and the teeth cover is expensive. Furthermore, users will feel uneasy.

SUMMARY OF THE INVENTION

Accordingly, the primary object of the present invention is to provide a sleep silencer, wherein the user only holds the sleep silencer in the mouth, the snore can be eliminated and thus the user can sleep comfortably.

To achieve above objects, the present invention provides a sleep silencer for eliminating snore by holding it in the mouth. The sleep silencer comprises a hollow tube which includes a front tube and a rear tube. One end of the front tube has an opening. A periphery of one distal end of the rear tube has a safety ring enclosing the periphery thereof. A ball stop is installed at a center of the opening of the front tube. Two sides of the ball stop are formed with respective turbulent devices which are adhered to an inner wall of the front tube so as to buffer the air in the front tube.

The various objects and advantages of the present invention will be more readily understood from the following detailed description when read in conjunction with the appended drawing.

DETAILED DESCRIPTION OF THE PREFERRED EMBODIMENTS

Figure 1:
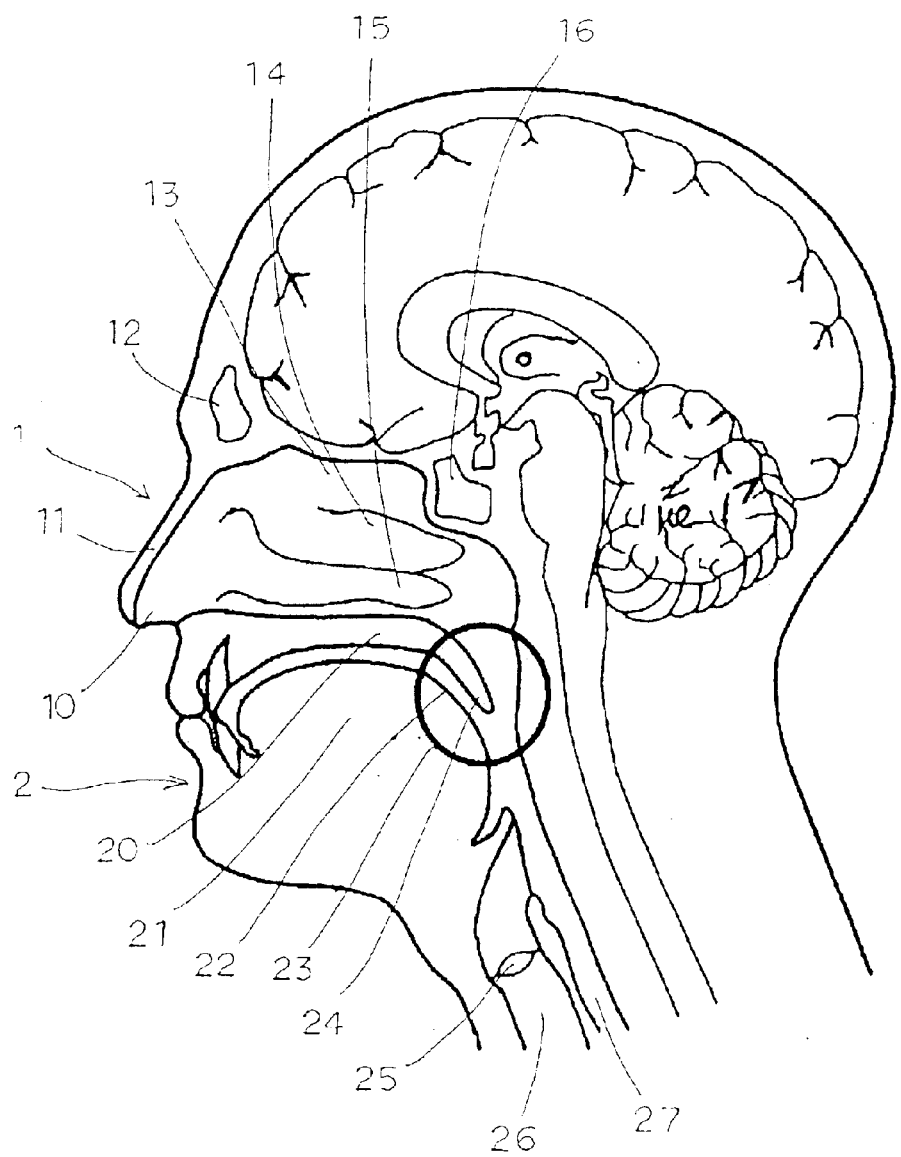
FIG. 1 is a structural schematic view showing the nose and mouth of a person.
Figure 2:
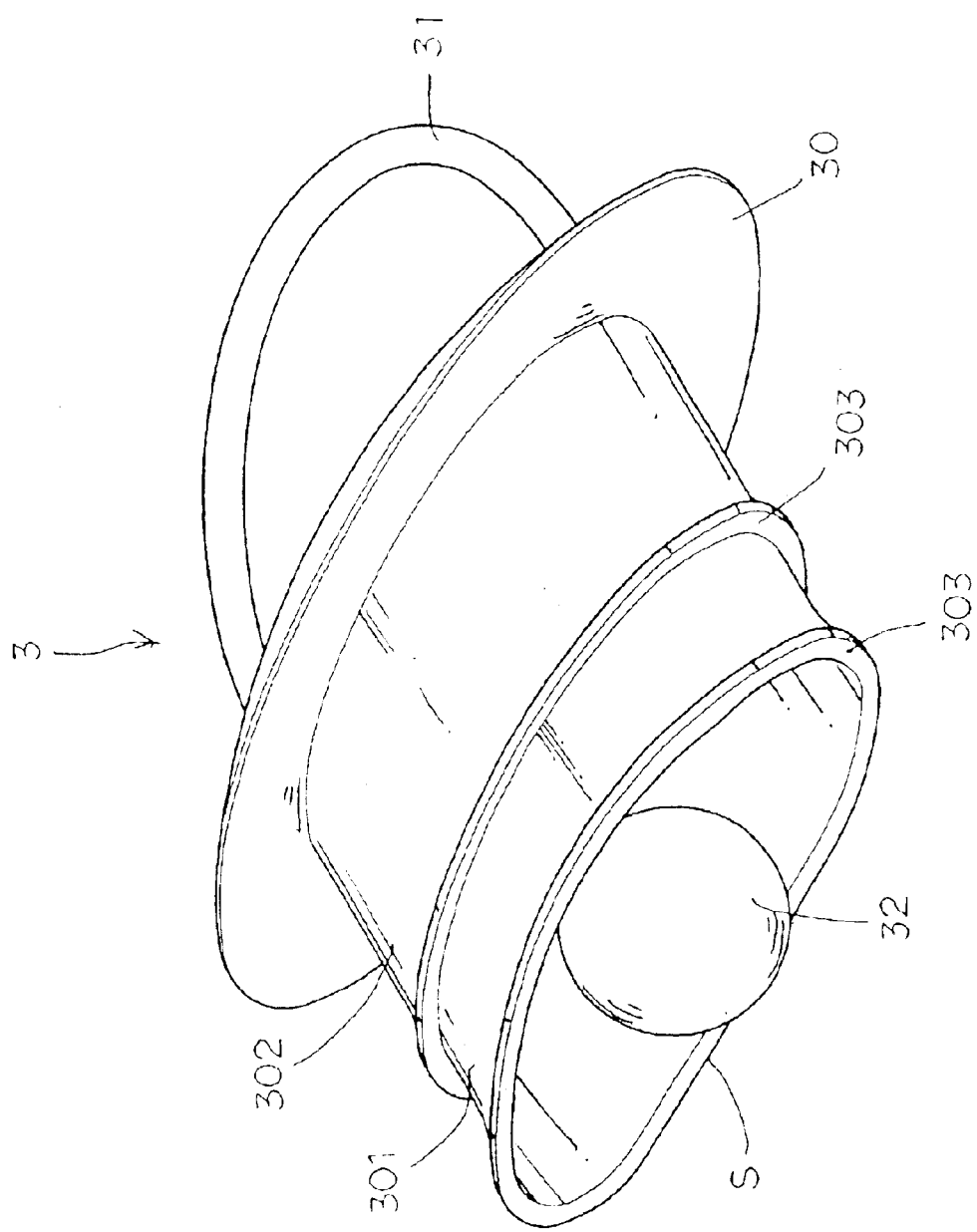
FIG. 2 is a schematic perspective view of the sleep silencer of the present invention.
Figure 3:
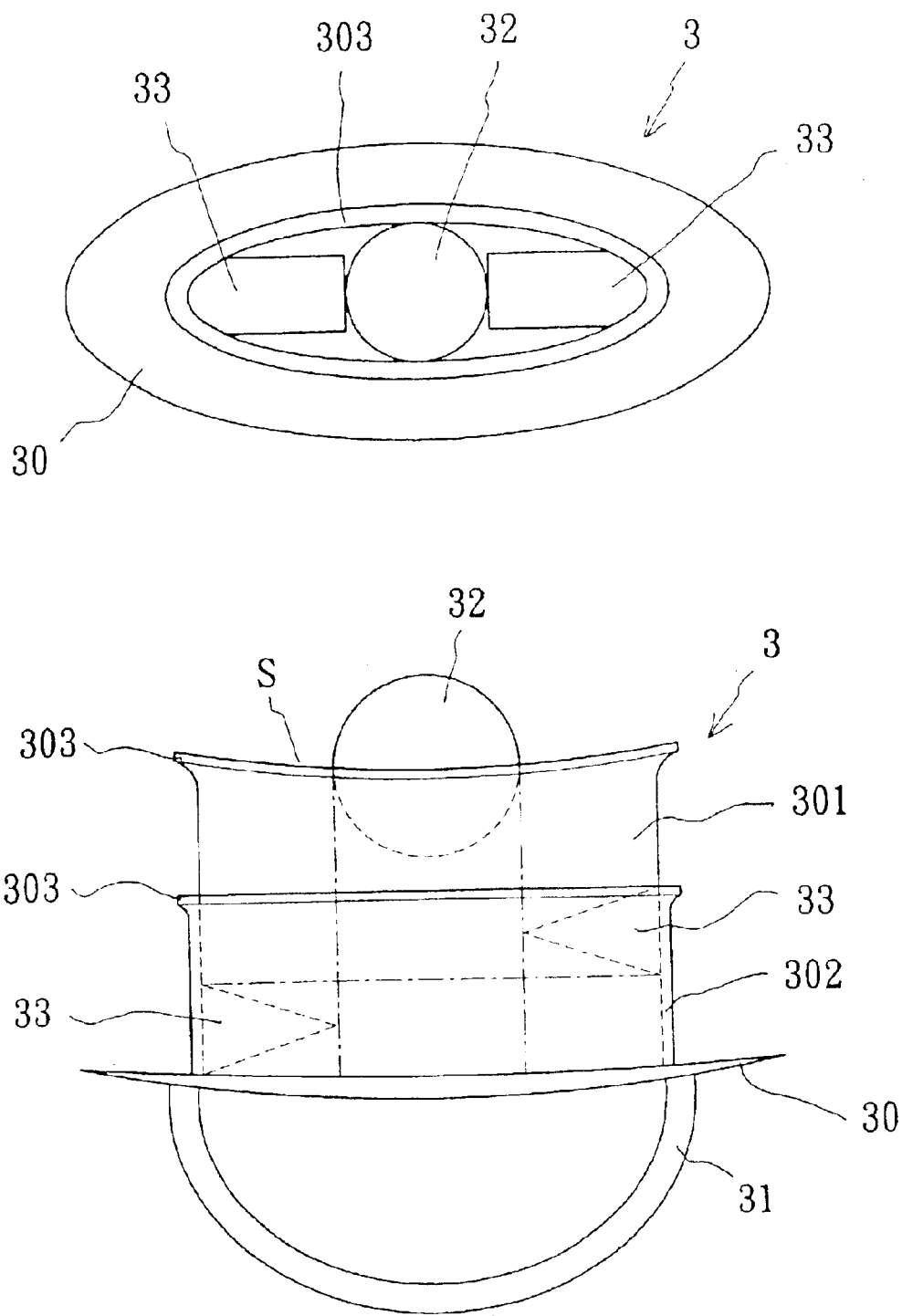
FIG. 3 is an upper and plane views of the sleep silencer of the present invention.

Referring to FIGS. 2 and 3, the sleep silencer of the present invention is illustrated. The sleep silencer can suppress snore effectively.

The sleep silencer 3 is a hollow tube made of soft elastic material, such as silicone (which is poisonless so that the sleep silencer 3 is safe; health-protected and make the user feel comfortable). A periphery of the sleep silencer 3 has a step-like shape so as to be divided into a front tube 301 and a rear tube 302. Predetermined positions of the front tube 301 and rear tube 302 are formed with respective flanges 303 for enhancing the elasticity thereof.

One end of the front tube 301 has an opening. The front tube 301 at the opening is formed with a cambered side S. A periphery of one distal end of the rear tube 302 has a safety ring 30 enclosing the periphery so that the sleep silencer 3 of the present invention cannot be swallowed by mistake. A pull ring is installed to the safety ring 30. When the sleep silencer 3 is not used, the sleep silencer 3 can not take down and is suspended by hanging from the pull ring.

Figure 4:
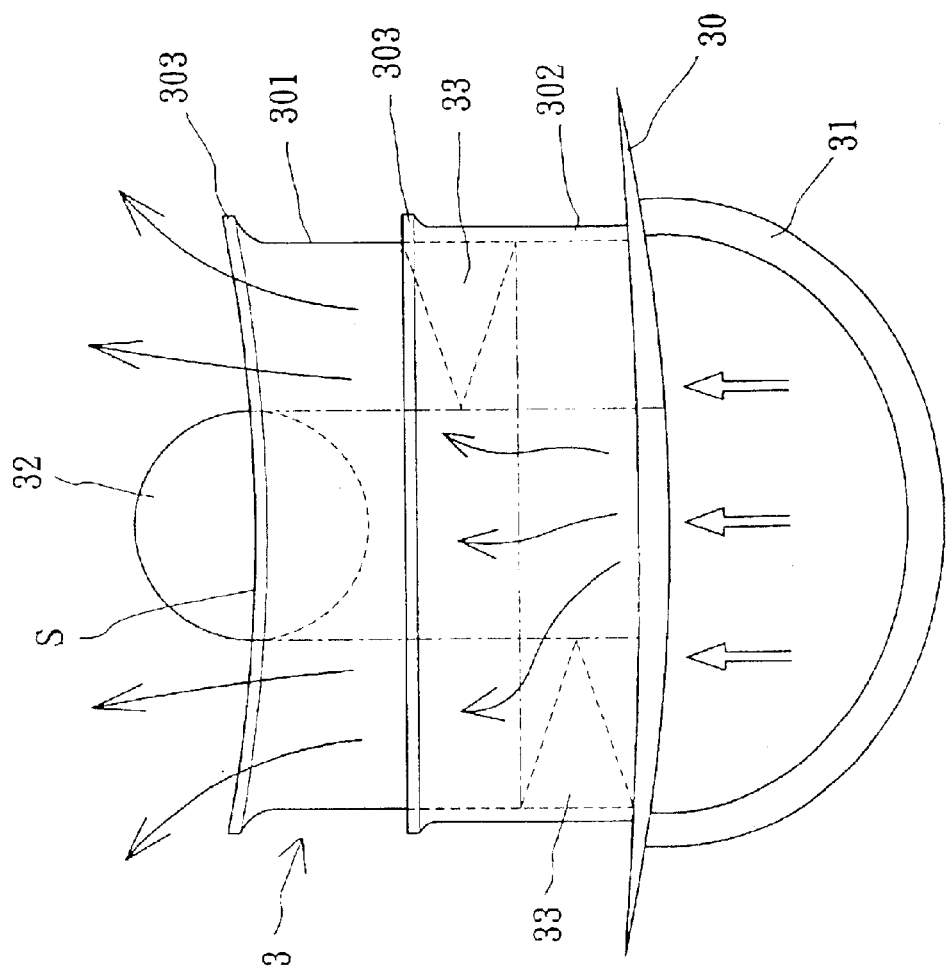
FIG. 4 is a schematic view showing the plane structure and air flow of the sleep silencer of the present invention.

A ball stop 32 is installed at a center of the opening of the front tube 301 for avoiding the tongue to insert into the front tube 301 carelessly. Two sides of the ball stop 32 are formed with respective turbulent devices 33 which are adhered to an inner wall of the front tube 301 so as to buffer the air in the front tube 301, as shown in FIG. 4. The lengths of the ball stop 32 and the turbulent devices 33 are about one thirds of the diameter of the front tube 301. The turbulent device has a shape selected from wing shapes, cell shapes, lattices, S shapes, streamline shapes, and spiral shapes.

In the present invention, the sleep silencer 3 is made of elastic material, such as silicone. This is because when a person is in sleep, the elastic material will expand the oral cavity so as to drive the platysma muscle, mylohyoid muscle, masseter muscle, digastric muscle, digastric muscle to extend. Since the muscle of the tongue is connected to the anterior palactine arch, throat muscle, pharyngeal wall of the lower jaw, the muscle of the lower jaw will be tightened. As a result, the mucous membrane of the respiratory passage will rise and the tongue moves forwards so that the respiratory passage is unobstructed. That is to say, the surplus tension must be over the retraction force of the tongue so that the tongue will not move downwards to hinder the respiratory passage and thus the snore can be cancelled.

The user of the sleep silencer 3 of the present invention will be described here.

Figure 5:
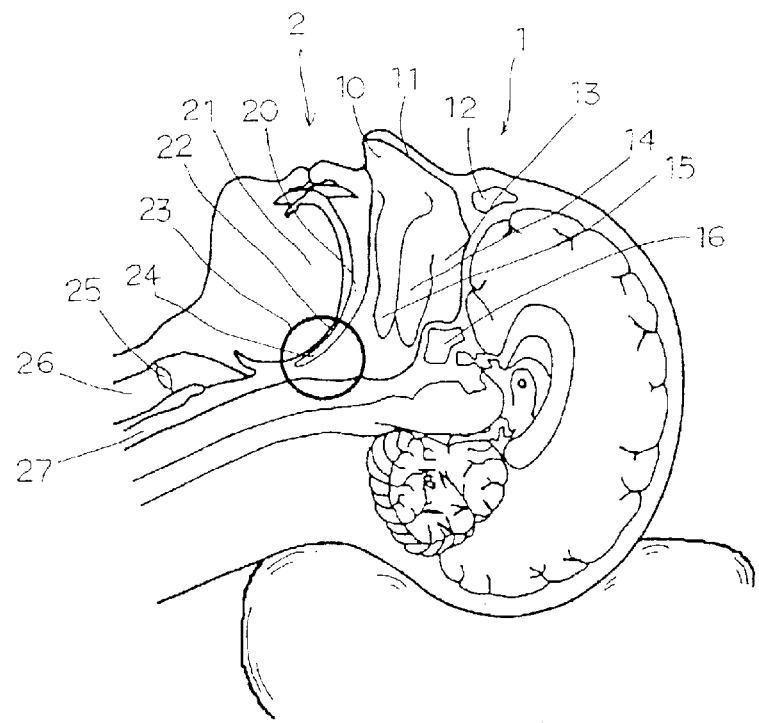
FIGS. 5A and 5B are schematic view showing the mouth constructions of a person using a sleep silencer of the present invention and without using a sleep silencer.
Figure 5:
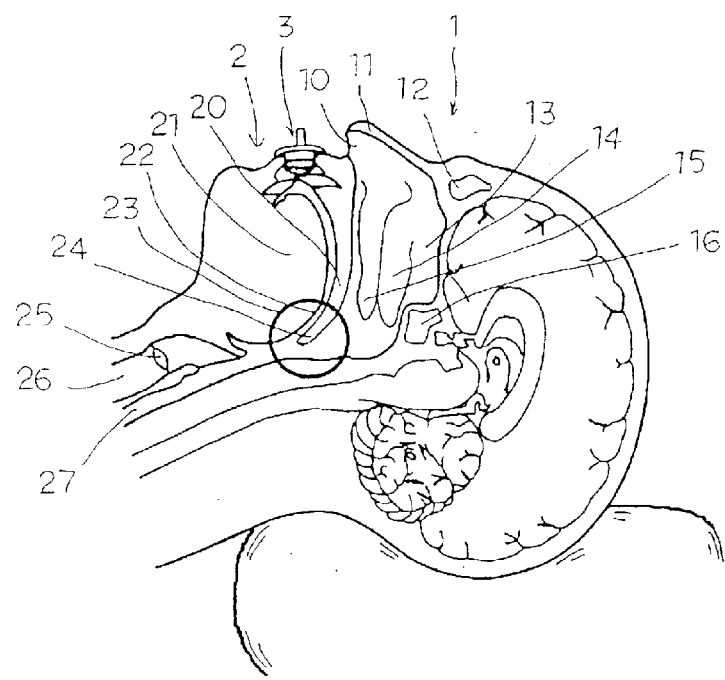

Referring to FIG. 5A, in this case, no sleep silencer is used. The soft palate 20, tongue 21, pharyngeal wall 22, anterior palactine arch 23, uvula 24, etc., in the oral cavity will become loose and droops so that the respiratory passage become narrow or stops. Thus sucked air can not flow successfully. When breathing, air will flow into the nose 1 or throat to move forwards. When air in the respiratory passage is rubbed with the mucous membrane of the respiratory passage, the mucous membrane of the respiratory passage will vibrate so as to induce snore.

Referring to FIG. 5B, when a person holds the sleep silencer 3 in the mouth in sleep, the lower jaw will expand so that the resistance force of the tongue 21 will increase. As a result, the respiratory passage and mucous membrane of the oral cavity will rise so that the soft palate 20, tongue 21, pharyngeal wall 22, anterior palactine arch 23, uvula 24, etc., in the oral cavity will move forwards to drive the platysma muscle, mylohyoid muscle, masseter muscle, digastric muscle, digastric muscle to expand. Since the muscle of the tongue is connected to the anterior palactine arch, throat muscle, pharyngeal wall of the lower jaw, the muscle of the lower jaw will be tightened. Thereby, no snore occurs.

In the present invention, the use of the sleep silencer 3 is adjusted according to the level of snore of the user. If the snore is slight, the user only needs to hold the front tube 301 of the sleep silencer 3. Then, the tongue 21 can firmly hold a lower edge f the front tube 301 and the flange 303 by using the elastic restoring force thereof. Thereby, the tongue 21 will not droop. If the snore voice is at a middle level, the mouth most holds the sleep silencer 3 to the rear tube 302. Since the rear tube 302 is higher than the front tube 301 and thus has a larger restoring force. Similarly, when the snore voice is strong, the sleep silencer 3 rotates through 90 degrees and then is held in mouth, but only the front tube 301 is held. If the snore voice is very great, it is necessary to hold to the rear tube 302 so as to suppress the snore.

Thereby, by the present invention, conventional techniques, such as surgery, syringing and drugging are unnecessary. Moreover, electronic assistant can not be used. It is only necessary to hold the sleep silencer 3 into mouth. Thus, the operation is easy and convenient. Moreover, user will feel easy and comfortable.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A sleep silencer for eliminating snore by holding the sleep silencer in a mouth; comprising:

a hollow tube including a front tube and a rear tube; one end of the front tube having an opening; a periphery of one distal end of the rear tube far away from the front tube having a safety ring; and a ball stop installed at a center of the opening of the front tube; two sides of the ball stop being formed with respective turbulent devices which are adhered to an inner wall of the front tube so as to buffer air within the front tube;

predetermined positions of the front tube and rear tube are formed with respective flanges; wherein the lower edge of the front tube is adapted to hold a patient's tongue firmly between the lower edge and the flange by the elastic restoring of the front tubes.

2. The sleep silencer as claimed in claim 1, wherein the sleep silencer is made of soft elastic material.

3. The sleep silencer as claimed in claim 1, wherein the sleep silencer is made of silicone.

4. The sleep silencer as claimed in claim 1, wherein the turbulent device has a shape selected from wing shapes, cell shapes, lattices, S shapes, streamline shapes, spiral shapes.

* * * * *